(12) United States Patent
Tsuchiya

(10) Patent No.: US 9,561,013 B2
(45) Date of Patent: Feb. 7, 2017

(54) MOVABLE RADIOGRAPHING APPARATUS AND MOVABLE RADIATION GENERATING APPARATUS HAVING WIRELESS COMMUNICATION

(71) Applicant: CANON KABUSHIKI KAISHA, Tokyo (JP)

(72) Inventor: Keiji Tsuchiya, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 16 days.

(21) Appl. No.: 14/711,666

(22) Filed: May 13, 2015

(65) Prior Publication Data

US 2015/0327833 A1  Nov. 19, 2015

(30) Foreign Application Priority Data

May 16, 2014  (JP) ................................. 2014-102586

(51) Int. Cl.
*H05G 1/02* (2006.01)
*A61B 6/00* (2006.01)

(52) U.S. Cl.
CPC ............... *A61B 6/56* (2013.01); *A61B 6/4405* (2013.01); *A61B 6/4411* (2013.01); *A61B 6/4435* (2013.01); *A61B 6/4458* (2013.01); *A61B 6/563* (2013.01); *A61B 6/4233* (2013.01); *A61B 6/467* (2013.01)

(58) Field of Classification Search
CPC ....... A61B 6/56; A61B 6/4411; A61B 6/4405; A61B 6/4458; A61B 6/4435; A61B 6/563; A61B 6/4233; A61B 6/467

USPC ......................................... 378/198, 204, 210
See application file for complete search history.

(56) References Cited

U.S. PATENT DOCUMENTS

| 2009/0016492 | A1* | 1/2009 | Tsuchiya | A61B 6/542 |
| | | | | 378/98.9 |
| 2010/0202589 | A1* | 8/2010 | Ohta | A61B 6/4233 |
| | | | | 378/98 |
| 2011/0311026 | A1* | 12/2011 | Lalena | A61B 6/4405 |
| | | | | 378/98.5 |
| 2013/0010928 | A1* | 1/2013 | Hannon | A61B 6/4405 |
| | | | | 378/98 |

FOREIGN PATENT DOCUMENTS

| JP | 2001-224579 A | 8/2001 |
| JP | 2011-056170 A | 3/2011 |
| JP | 2011-083649 A | 4/2011 |
| JP | 2013-017816 A | 1/2013 |

* cited by examiner

*Primary Examiner* — Michael Maskell
(74) *Attorney, Agent, or Firm* — Canon USA Inc., IP Division

(57) ABSTRACT

A movable radiographing apparatus has a wireless communication function and includes a radiation generating unit including a radiation source, an arm portion configured to support the radiation generating unit, a support pillar configured to support the arm portion, and a moving unit configured to support the support pillar and including a GUI to be operated by the user. The movable radiographing apparatus further includes a connector unit to and from which an external antenna for wireless communication is attachable and detachable, wherein the connector unit is provided on at least one of the radiation generating unit, the arm portion, the support pillar, and the moving unit.

9 Claims, 9 Drawing Sheets

FIG. 8

| CHANNEL | ESSID | dBm |
|---|---|---|
| 2 | OTHER10 | −60 |
| 3 | PORT01 | −40 |
| 5 | OTHER11 | −70 |
| 7 | OTHER12 | −80 |
| 10 | OTHER13 | −70 |

MOVABLE RADIOGRAPHING APPARATUS AND MOVABLE RADIATION GENERATING APPARATUS HAVING WIRELESS COMMUNICATION

BACKGROUND OF THE INVENTION

Field of the Invention

The present invention relates to a wirelessly communicable movable radiographing apparatus and a movable radiation generating apparatus.

Description of the Related Art

Japanese Patent Application Laid-Open Nos. 2011-83649 and 2011-56170 disclose movable radiographing apparatuses. A mobile radiographing apparatus is used for patients who have difficulty in moving or cannot be moved in hospitals. A movable radiation generating apparatus is used in home medical treatment for patients who have difficulty in visiting a hospital, emergency medical treatment outside a hospital, for example. Further, Japanese Patent Application Laid-Open No. 2001-224579 discusses a wirelessly communicable flat panel detector (FPD) which is advantageously used with mobile radiographing apparatuses for used for patients who have difficulty in moving. Furthermore, Japanese Patent Application Laid-Open No. 2013-17816 discusses a movable radiographing apparatus for stable wireless communication in a case where a wirelessly communicable FPD is used in the movable radiographing apparatus. "Stable wireless communication" is wireless communication in which wireless communication between the movable radiographing apparatus and the FPD is reliable and efficient without wireless communication being often disconnected or data transfer speed of the wireless communication being decreased.

Various solutions purported to achieve stable wireless communication have been proposed. For example, a plurality of antennas is provided at predetermined positions within or on a surface of a movable radiographing apparatus. Japanese Patent Application Laid-Open No. 2013-17816 discusses such a configuration in which a plurality of antennas is provided under a display and/or near a bottom of a base unit. In this configuration, however, the positions and orientation of the antennas are limited (fixed). Thus, although the configuration can include a plurality of antennas, it is difficult to ensure stable wireless communication at all times. Thus, non stable wireless communication can occur not only in movable radiographing apparatuses but also in movable radiation generating apparatuses depending on the environment where these are used.

SUMMARY OF THE INVENTION

The present invention is directed to a movable radiographing apparatus and a movable radiation generating apparatus capable of performing radiographing while performing stable wireless communication.

According to an aspect of the present invention, a movable radiographing apparatus and a movable radiation generating apparatus that have a wireless communication function include a connector unit to and from which an external antenna for wireless communication is attachable and detachable. According to another aspect of the present invention, a movable radiographing apparatus and a movable radiation generating apparatus that have a wireless communication function are capable of performing radiographing while performing stable wireless communication.

Further features of the present invention will become apparent from the following description of exemplary embodiments with reference to the attached drawings.

BRIEF DESCRIPTION OF THE DRAWINGS

FIG. 8 is a table illustrating radio field intensities of a wireless LAN of respective channels, which are received by a portable computer.

DESCRIPTION OF THE EMBODIMENTS

Various exemplary embodiments, features, and aspects of the invention will be described in detail below with reference to the drawings.

A first exemplary embodiment of the present invention will be described below. In the present exemplary embodiment, a movable radiographing apparatus having a wireless communication function will be described as an example of a movable radiographing apparatus. Further, a wireless local area network (LAN) defined by the IEEE 802.11 protocol will be described as an example of a wireless communication method.

Figure 1:
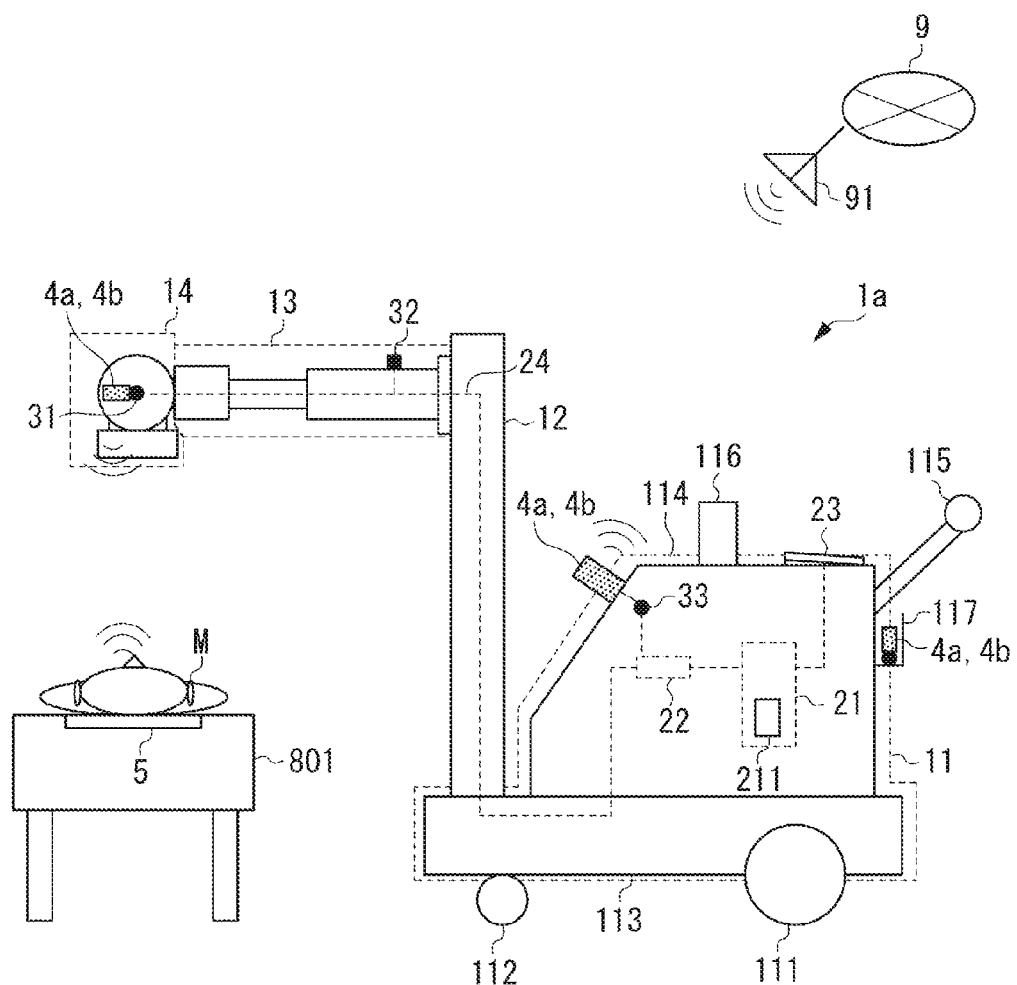
FIG. 1 is a schematic block diagram illustrating a movable radiographing apparatus according to a first exemplary embodiment.

FIG. 1 is a block diagram illustrating a schematic configuration of a movable radiographing apparatus 1a according to the present exemplary embodiment and a state of the movable radiographing apparatus 1a in use. In radiographing, the movable radiographing apparatus 1a and a flat panel detector (FPD) 5 are used. The FPD 5 is wirelessly communicable with the movable radiographing apparatus 1a. FIG. 1 illustrates an example case where a subject M lying on a bed 801 in a hospital room is radiographed. Further, the movable radiographing apparatus 1a can access an in-hospital network 9 such as a hospital information system (HIS), a radiology information system (RIS), or a picture archiving and communication system (PACS) via the wireless LAN.

The movable radiographing apparatus 1a includes a moving unit 11, a support pillar 12, an extendable arm portion 13, and a radiation generating unit 14 including a radiation source. The moving unit 11 includes a frame 113 (chassis) and a box-shaped casing 114 disposed on an upper side of the frame 113. Rear wheels 111 and front wheels 112 are rotatably attached to the frame 113. The support pillar 12 is supported by the frame 113 of the moving unit 11. The arm portion 13 supports the radiation generating unit 14. The arm portion 13 is supported by the support pillar 12 and configured to be extendable horizontally. The radiation generating unit 14 includes a housing (not illustrated) and a collimator (not illustrated). The housing includes a built-in radiation source (e.g., radiation tube). The radiation generating unit 14 may include an X-ray generator, and the radiation source may include an X-ray tube which emits X-ray radiation. The collimator narrows the irradiation field of radiation emitted by the radiation source. For convenience of description, the side of the movable radiographing apparatus 1a on which the support pillar 12 is provided (left hand side in FIG. 1) is referred to as a front side, and the opposite side (right hand side in FIG. 1) is referred to as a rear side.

The casing 114 of the moving unit 11 includes a handle 115 and an arm fixing unit 116. The user uses the handle 115 to move the movable radiographing apparatus 1a. The handle 115 is provided at, for example, a rear part of the casing 114 of the moving unit 11. The arm fixing unit 116 is a member that fixes the arm portion 13 in a retracted state at the time of storing the radiation generating unit 14. The arm fixing unit 116 is provided at, for example, an upper part of the casing 114 of the moving unit 11.

A control unit 21 and an access point 22 of the wireless LAN are provided within the casing 114 of the moving unit 11. The control unit 21 controls the movable radiographing apparatus 1a. The access point 22 of the wireless LAN interconnects the wireless LAN and a wired LAN. Further, the control unit 21 and the access point 22 are connected via the wired LAN. Further, the control unit 21 includes a storage unit 211 configured to store antenna information described below.

A graphical user interface (GUI) 23, which is an example of an operation unit, is provided on an upper part of the casing 114 of the moving unit 11. The GUI 23 is operated by the user and used to display captured images such as captured radiation images and various types of information. The user can check information displayed on the GUI 23 and operate the GUI 23 to set parameters for the radiographing. A touch panel type GUI including a display panel and a touch panel is used as the GUI 23. The GUI 23 is connected to the control unit 21 by wired connection via, for example, a digital visual interface (DVI) to send and receive signals to and from the control unit 21.

The movable radiographing apparatus 1a includes connector units 31, 32, and 33 provided at a plurality of positions, and antenna storing portion 117. A plurality of external antennas 4a and 4b (which will be described below) are arranged in the antenna storing portion 117. For wireless communication, the antennas 4a and 4b can be attached to and removed from the connector units 31, 32, and 33. In the present exemplary embodiment, the movable radiographing apparatus 1a including the connector units 31, 32, and 33 provided at three positions will be described. Herein, the connector units 31, 32, and 33 are provided at the radiation generating unit 14, the arm portion 13, and the moving unit 11, respectively. Further, FIG. 1 illustrates a state in which the external antennas 4a and 4b for wireless communication are attached to the connector units 31 and 33, respectively, while no external antenna for wireless communication is attached to the connector unit 32. However, the movable radiographing apparatus 1a needs to include any of the connector units 31, 32, and 33 at one or more positions, and the number of the connector units 31, 32, and 33 is not limited. For example, a coaxial cable connector is used as the connector units 31, 32, and 33. The connector units 31, 32, and 33 are connected to the access point 22 of the wireless LAN by wired connection using, for example, a coaxial cable 24. While FIG. 1 illustrates a configuration in which the coaxial cable 24 is arranged within the support pillar 12 and the arm portion 13, the route of the coaxial cable 24 is not limited to the route illustrated in FIG. 1. Further, the moving unit 11 includes an antenna storing portion 117 for storing the attachable/detachable external antennas 4a and 4b. FIG. 1 illustrates a state in which the external antennas 4a and 4b are stored in the antenna storing portion 117.

Figure 2A:
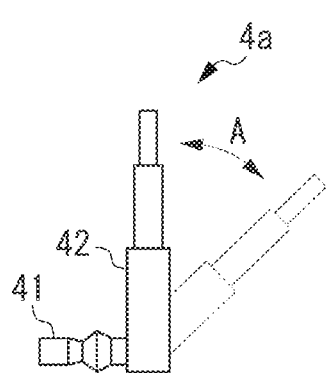
FIGS. 2A and 2B are schematic diagrams each illustrating an attachable/detachable external antenna.
Figure 2B:
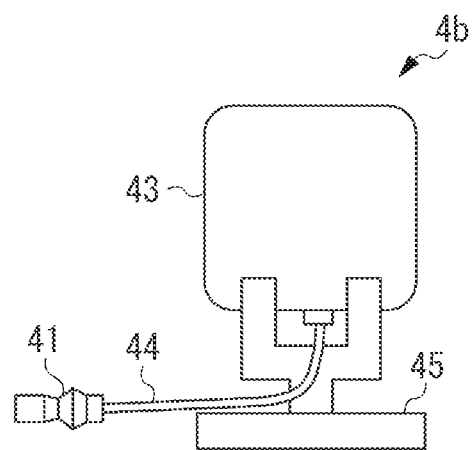

An example of the external antennas 4a and 4b for wireless communication that are attachable to and detachable from at least one of the connector units 31, 32, and 33, is described with reference to FIGS. 2A and 2B. FIGS. 2A and 2B each illustrate an example of an external antenna for wireless communication that is attachable to and detachable from the connector units 31, 32, and 33. More specifically, FIG. 2A illustrates a dipole antenna 4a, which is an example of an omnidirectional antenna without a cable. FIG. 2B illustrates a diversity antenna 4b, which is an example of a directional antenna with a cable. The dipole antenna 4a includes a connector unit 41 and an antenna unit 42. The connector unit 41 is a portion that is attachable to and removable from any one of the connector units 31, 32, and 33. For example, a coaxial cable connector is used as the connector unit 41. The angle of the antenna unit 42 with respect to the connector unit 41 can be changed by moving the antenna unit 42 in a direction indicated by an arrow A. The diversity antenna 4b includes a connector unit 41, an antenna unit 43, a cable unit 44, and a support or fixing unit 45. A magnet, for example, is embedded in the fixing unit 45 so that the diversity antenna 4b can be affixed in an arbitrary position on the movable radiographing apparatus 1a by the magnetic force of the magnet. In the diversity antenna 4b, the connector unit 41 and the antenna unit 43 are connected by the cable unit 44 having flexibility. The external antennas 4a and 4b are selectively attachable and detachable via the connector unit 41 to and from any of the connector units 31, 32, and 33 provided at a plurality of positions of the movable radiographing apparatus 1a.

The attachable/detachable external antennas 4a and 4b are not limited to the dipole antenna 4a and the diversity antenna 4b illustrated in FIGS. 2A and 2B. For example, the wireless LAN protocols defined by IEEE 802.11 include methods using radio waves of the 2.4 GHz or 5 GHz band. Therefore, for the wireless LAN protocols, there are an antenna that is compatible with the 2.4 GHz band, an antenna that is compatible with the 5 GHz band, and an antenna that is compatible with the 2.4 GHz and 5 GHz bands. Thus, the configurations of the external antennas 4a and 4b may be selected as appropriate for the wireless LAN method with which the movable radiographing apparatus 1a is compatible. Further, whether to use an omnidirectional antenna or a directional antenna and whether to use an antenna with a cable or an antenna without a cable can be selected as appropriate.

The FPD 5 wirelessly communicates with the control unit 21 via the external antennas 4a and 4b over the wireless LAN. Then, the FPD 5 transfers image data of a captured radiographic image to the control unit 21 over the wireless LAN. When receiving the image data of the radiographic image from the FPD 5, the control unit 21 performs image processing and the like on the received image data and then displays the image data on the GUI 23. At this time, the control unit 21 adds information such as a hospital room number, position of the bed in the hospital room, patient information, radiographing conditions, and imaged site information to the image data of the captured radiographic image. In addition to the foregoing information, the control unit 21 also adds antenna information to the image data of the captured radiographic image. The antenna information to be added to the image data of the radiographic image includes information about the frequency of the wireless LAN, channels, radio field intensity of the wireless LAN, the positions of the connector units 31, 32, and 33 to which the external antennas 4a and 4b are attached, and the types and orientations of the external antennas 4a and 4b.

Thereafter, if, for example, the user determines that the captured radiographic image is acceptable, the user performs an operation to transfer the image data of the captured radiographic image to the PACS or the like, by using the GUI 23. In response to the operation performed by the user, the control unit 21 transfers the image data of the captured radiographic image to the in-hospital network 9 such as the PACS by use of the wireless LAN via the external antennas 4a and 4b and the antenna 91.

An example of a method for setting the information about the frequency of the wireless LAN, channels, and radio field intensity of the wireless LAN at which the communication state of the wireless LAN is stable, is described. In the present exemplary embodiment, the wireless LAN communication according to the IEEE802.11.b protocol will be described as an example. In the wireless LAN communication according to the IEEE 802.11.b protocol, the frequency band of 2.4 GHz is used, and 14 channels CH1 to CH14 are available for use. The bands of the channels are separated by 5 MHz. Further, the 22 MHz band is used in one wireless LAN. Accordingly, to prevent a plurality of wireless LANs from interfering with one another, it is desirable to separate the plurality of wireless LANs by at least 5 channels apart and communicate.

The user attaches the connector units 41 of the attachable/detachable external antennas 4a and 4b to any of the connector units 31, 32, and 33 provided at a plurality of positions. Further, the user operates the support pillar 12 and the extendable arm portion 13 of the movable radiographing apparatus 1a to move the radiation generating unit 14 to a position for capturing a radiographic image. Further, the user places the FPD 5 on the rear side of the subject M seen from the radiation generating unit 14 side (position where radiations having passed through the subject M enter). Then, the user uses the GUI 23 to perform an operation to measure the radio field intensity of the wireless LAN around the movable radiographing apparatus 1a. Upon detecting the operation, the control unit 21 instructs the access point 22 to measure the radio field intensity and an extended service set identifier (ESSID) of each channel. The access point 22 measures the radio field intensity and the ESSID of each channel, and returns the results to the control unit 21. The control unit 21 displays the measurement results on the GUI 23. Then, the control unit 21 periodically repeats the foregoing process.

Figure 3:
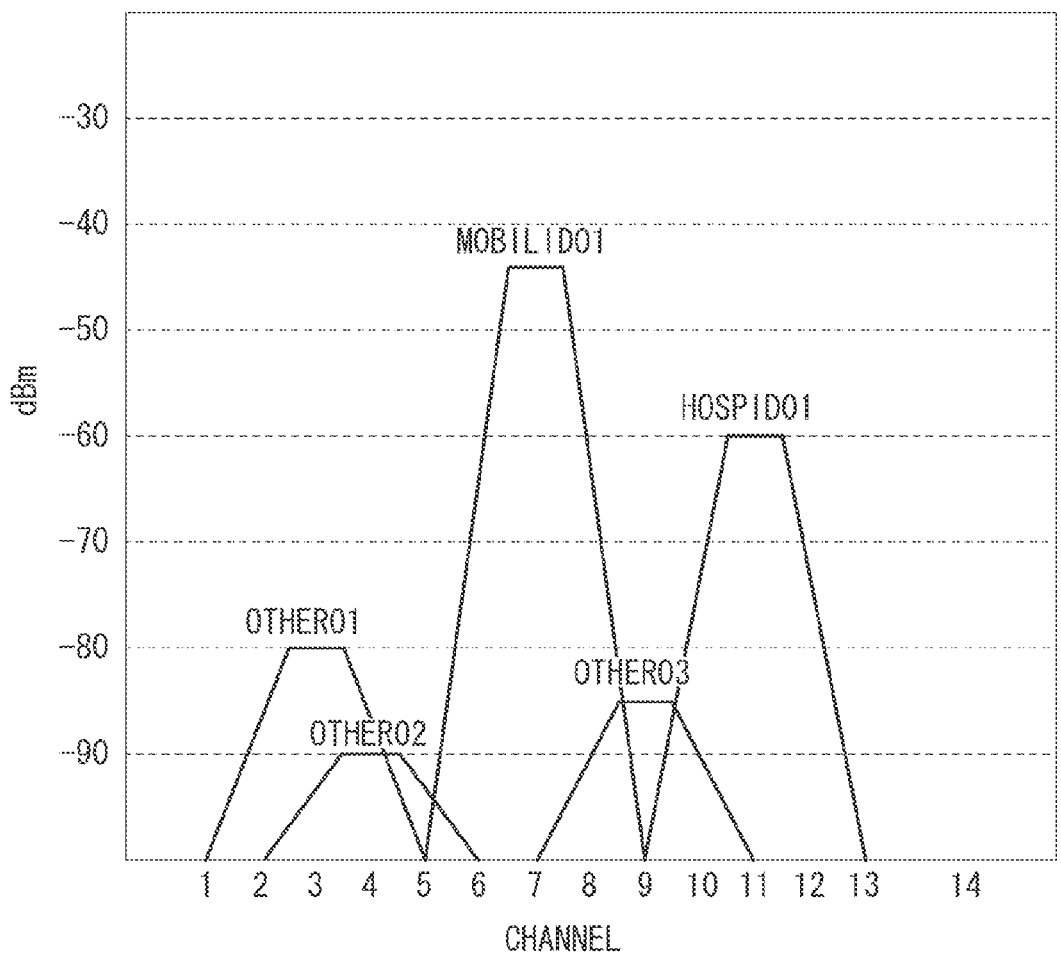
FIG. 3 illustrates a display example of measurement results of radio field intensity of a wireless local area network (LAN) of respective channels that were measured by an access point.

FIG. 3 illustrates an example of the measurement results of the radio field intensity of the wireless LAN of the respective channels, which are displayed on the GUI 23. On the screen of the GUI 23, the horizontal axis represents channels, and the vertical axis indicates radio field intensity. A larger number along the vertical axis indicates that a higher radio field intensity can be received by the access point 22. "MOBILID" denotes the ESSID name of the FPD 5, and "HOSPID01" denotes the ESSID name for connecting to the in-hospital network 9. Further, "OTHER01," "OTHER02," and "OTHER03" each denote the ESSID names of wireless apparatuses having no relation to the movable radiographing apparatus 1a, the FPD 5, and the in-hospital network 9. In the example illustrated in FIG. 3, the center channel in the wireless LAN communication between the movable radiographing apparatus 1a and the FPD 5 is the channel CH7, and the measurement result of the radio field intensity thereof is −45 dBm. Further, the center channel in the wireless LAN communication between the movable radiographing apparatus 1a and the in-hospital network 9 is the channel CH11, and the measurement result of the radio field intensity thereof is −60 dBm. Further, the center channel for another wireless apparatus "OTHER01" is the channel CH3, and the measurement result of the radio field intensity thereof is −80 dBm. Further, the center channel for yet another wireless apparatus "OTHER02" is the channel CH4, and the measurement result of the radio field intensity thereof is −90 dBm. Further, the center channel for yet another wireless apparatus "OTHER03" is the channel CH9, and the measurement result of the radio field intensity thereof is −85 dBm.

In the present exemplary embodiment, as an example, two external antennas 4a and 4b are attached to each of the connector units 31 and 33 provided at two positions while neither external antenna 4a nor 4b is attached to the remaining connector unit 32. A change in the orientations of the external antennas 4a and 4b causes a change in the measurement results of the radio field intensity of the wireless LAN for the channels that are displayed on the GUI 23. Thus, when the radio field intensities of other wireless apparatuses having no relation to the radiography are high, the user changes the position and/or the orientation of one or both of the two external antennas 4a and 4b attached to each of the connector units 31 and 33 provided at two positions. In this way, the radio field intensities of the other wireless apparatuses can be decreased. Further, as illustrated in FIG. 1, in a case where the wireless communication is unstable because a sufficiently high radio field intensity cannot be obtained with the two external antennas 4a and 4b, the user may further attach additional external antennas 4a and 4b to an available connector unit 32. The external antennas 4a and 4b can be provided freely in any position as long as smooth radiographing is not disturbed.

The user can arbitrarily set the types, positions, orientations, etc. of the external antennas 4a and 4b while checking the measurement results of the radio field intensity displayed on the GUI 23. Thus, the user sets the types, positions, orientations, etc. of the external antennas 4a and 4b to stabilize the communication state of the wireless LAN. Then, at the completion of the setting to stabilize the communication state of the wireless LAN, the user operates the GUI 23 to store the settings. In response to the operation, the control unit 21 stores in the storage unit 211 the information about the frequency, channel, and radio field intensity at which the communication state of the wireless LAN is stable.

Figure 4:
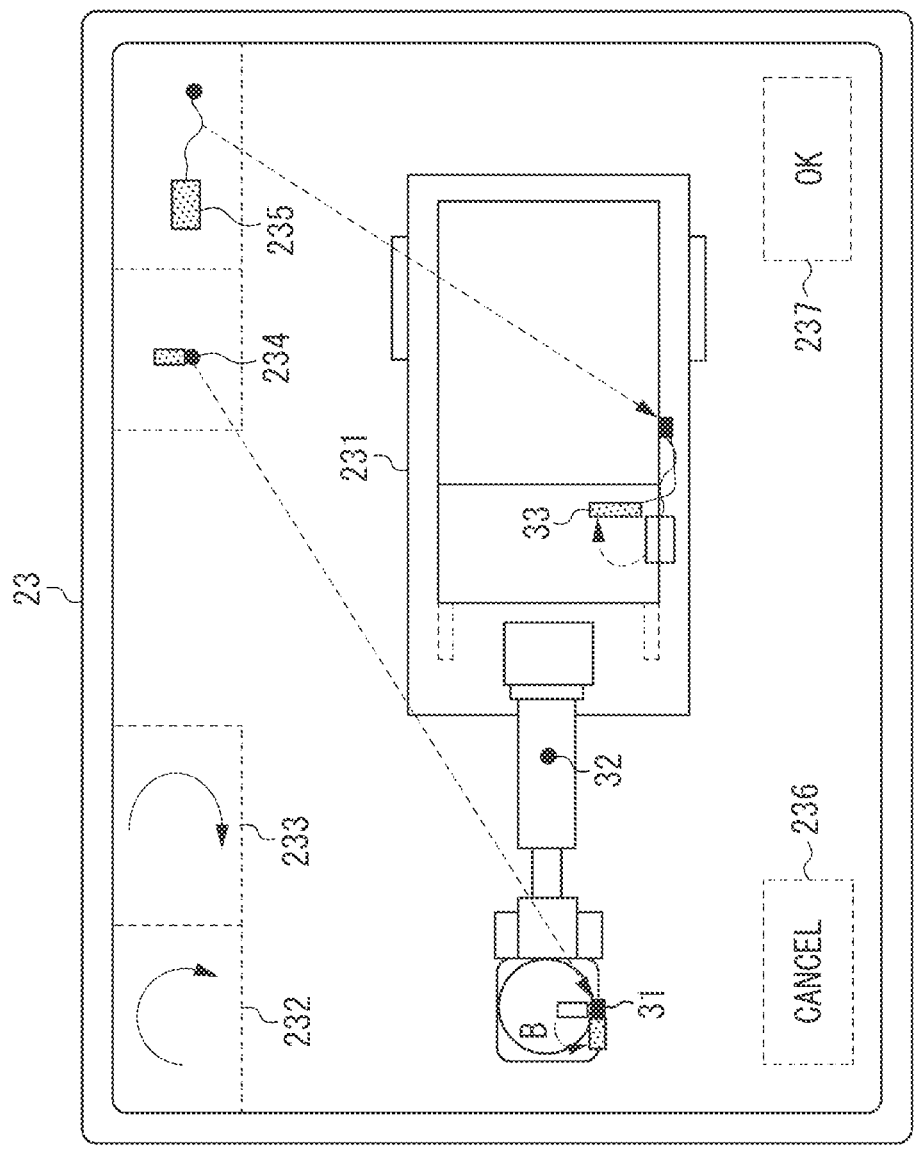
FIG. 4 illustrates an example of a display screen of a graphical user interface (GUI) at the time of setting antenna information.

When the setting of the positions and orientations of the external antennas 4a and 4b is completed, the user can set information about the positions of the connectors and the types and orientations of the attached antennas by use of the GUI 23. A method for setting the foregoing information will be described below with reference to FIG. 4. FIG. 4 illustrates an example of a screen displayed on the GUI 23 at the time of setting the antenna information. The user uses the screen displayed on the GUI 23 to set the information about the positions of the connector units 31, 32, and 33 to which the external antennas 4a and 4b are attached and the information about the types and orientations of the attached external antennas 4a and 4b. In the present exemplary embodiment, a case where the dipole antenna 4a, which is an example of an omnidirectional antenna, is attached to the connector unit 31, and the diversity antenna 4b, which is an example of a directional antenna, is attached to the connector unit 33 will be described. As illustrated in FIG. 4, the control unit 21 displays on the GUI 23 a radiographing apparatus object 231, which is a schematic top plan view of the movable radiographing apparatus 1a. Further, the control unit 21 displays arrow icons 232 and 233, each of which indicates a rotation, at an upper left portion of the GUI 23, external antenna icons 234 and 235 at an upper right portion, a cancel button 236 at a lower left portion, and an OK button 237 at a lower right portion.

When the user selects the arrow icon 232 (when a touch on the arrow icon 232 is detected), the control unit 21 rotates the radiographing apparatus object 231 clockwise. Further, when the arrow icon 233 is selected (when a touch on the arrow icon 233 is detected), the viewpoint from which the radiographing apparatus object 231 is viewed is moved downward. Accordingly, if the user repeats selection of the arrow icon 233, a side surface of the movable radiographing apparatus 1a gradually becomes visible.

The external antenna icons 234 and 235 respectively correspond to the dipole antenna 4a and the diversity antenna 4b illustrated in FIGS. 2A and 2B. Further, black circle portions of the external antenna icons 234 and 235 indicate the connector units 41 of the external antennas 4a and 4b. When the user selects and drags the external antenna icon 234 at the upper right portion, the control unit 21 moves the external antenna icon 234 according to the drag performed by the user. When the black circle portion of the external antenna icon 234 is dragged to the position of the connector unit 31, the control unit 21 recognizes that the connector unit 41 of the dipole antenna 4a is attached to the connector unit 31. Then, when the external antenna icon 234 is selected again and a drag operation to further rotate the external antenna icon 234 along the direction indicated by an arrow B is detected, the control unit 21 rotates the external antenna icon 234. Then, the control unit 21 recognizes, as the orientation of the antenna unit 42 of the attached dipole antenna 4a, the orientation of the external antenna icon 234 at the time of the completion of the drag operation to rotate the external antenna icon 234. Thus, the user drags the external antenna icon 234 so that the control unit 21 can recognize the connector unit 31 to which the dipole antenna 4a is attached and the orientation of the attached dipole antenna 4a. Similarly, when the external antenna icon 235 is selected and dragged to the position of the connector unit 32, the control unit 21 recognizes that the diversity antenna 4b is attached to the connector unit 32.

When the cancel button 236 displayed at the lower left portion is selected (touched), the control unit 21 cancels the aforementioned operations and the recognitions. Thus, when the user performs an erroneous operation, the user can cancel the erroneous operation by selecting the cancel button 236. When the OK button 237 is selected, the control unit 21 stores in the storage unit 211 the information about the positions of the connector units 31, 32, and 33, to which the external antennas 4a and 4b are attached, and the information about the types and orientations of the attached external antennas 4a and 4b. Thus, when the operation to make the settings of the external antennas 4a and 4b on the GUI 23 is completed, the user can confirm the settings by selecting the OK button 237.

Thereafter, when an operation performed by the user to give an instruction to execute radiographing is detected, the control unit 21 executes radiographing. Then, the control unit 21 adds information such as a hospital room number, a position of the bed in the hospital room, patient information, radiographing conditions, and imaged site information to the image data of the captured radiographic image to the image data of the captured radiographic image. In addition to the foregoing information, the control unit 21 also adds the antenna information to the image data of the captured radiographic image. The antenna information includes information about the frequency of the wireless LAN, channels, radio field intensity of the wireless LAN, the positions of the connector units 31, 32, and 33, to which the attachable/detachable external antennas 4a and 4b are attached, and the types and orientations of the attached external antennas 4a and 4b. Then, the control unit 21 stores in the storage unit 211 the image data to which the foregoing information is added. Further, in response to an operation performed by the user, if any, the control unit 21 transfers the image data of the radiographic image, to which the foregoing information is added, to the in-hospital network 9 such as the PACS by use of the wireless LAN.

Figure 5A:
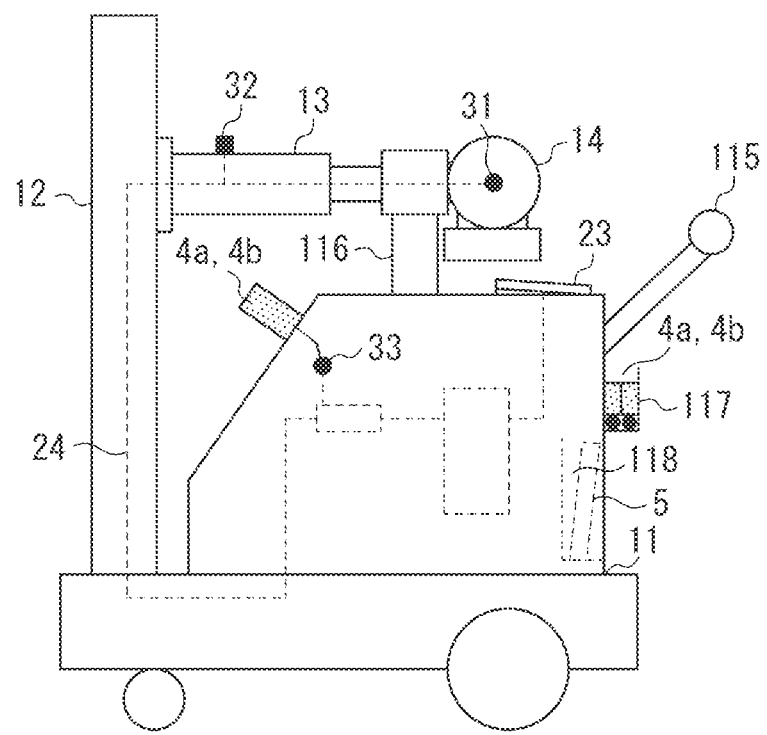
FIGS. 5A and 5B are schematic diagrams illustrating a state of a movable radiographing apparatus being moved.
Figure 5B:
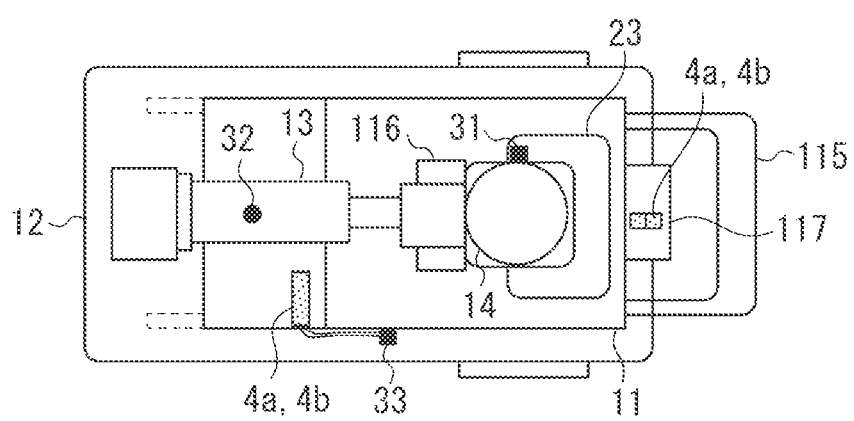

FIGS. 5A and 5B each schematically illustrate a state of the movable radiographing apparatus 1a when it is moved. FIG. 5A is a side view, and FIG. 5B is a plan view. At the time of moving the movable radiographing apparatus 1a, the user rotates the support pillar 12 toward the rear side to orient the arm portion 13 and the radiation generating unit 14 toward the rear side. Then, the arm portion 13 is contracted, lowered, and then fixed to the arm fixing unit 116. Further, the movable radiographing apparatus 1a includes an FPD storing unit 118 for storing the FPD 5. At the time of moving the movable radiographing apparatus 1a, the user stores the FPD 5 in the FPD storing unit 118. FIGS. 5A and 5B illustrate a state in which the FPD 5 is stored in the FPD storing unit 118 of the moving unit 11. Further, FIGS. 5A and 5B illustrate a state in which one set of external antennas 4a and 4b is attached to the connector unit 33 and two sets of external antennas 4a and 4b are stored in the antenna storing portion 117 is illustrated. The connector units 31, 32, and 33 to and from which the external antennas 4a and 4b are attachable and removable are provided at positions where the external antennas 4a and 4b can be attached and removed even when the arm portion 13 is fixed to the arm fixing unit 116.

Normally, the user operates the GUI 23 to receive from the in-hospital network and display information such as the hospital room in which radiographing is to be performed using the movable radiographing apparatus 1a, the position of the bed in the hospital room, subject information, information about a site to be radiographed. Then, the user operates the handle 115 to move the movable radiographing apparatus 1a to the place where radiographing is to be performed. When the external antennas 4a and 4b are stored in the antenna storing portion 117, the external antennas 4a and 4b do not disturb the smooth movement of the movable radiographing apparatus 1a. Further, the external antennas 4a and 4b can be provided at arbitrary positions. Thus, the external antennas 4a and 4b can be provided at arbitrary positions in such a manner that the external antennas 4a and 4b do not disturb the smooth movement of the movable radiographing apparatus 1a even when the external antennas 4a and 4b are attached to the connector units 31, 32, and 33.

After moving the movable radiographing apparatus 1a near the bed of the subject M to be radiographed, the user performs an operation to display on the GUI 23 the antenna information at the time of the previous radiographing performed at the same bed. In response to the operation, the control unit 21 reads from the in-hospital network 9 via the wireless LAN the antenna information at the time of the previous radiographing performed at the same bed and displays the read antenna information on the GUI 23. As described above, the antenna information includes information about the frequency of the wireless LAN, channels, radio field intensity of the wireless LAN, the positions of the connector units to which the attachable/detachable external antennas are attached, and the types and orientations of the attached external antennas (refers to FIGS. 3 and 4). Thus, the user can easily duplicate the same settings (the external antennas 4a and 4b to be used, the positions and orientations of the external antennas 4a and 4b, the connector units 31, 32, and 33 to which the external antennas 4a and 4b are to be attached) used in the previous radiographing performed at the same bed while checking the information displayed on the GUI 23. Since the storage unit 211 stores the settings at which the wireless communication is stable, the user can easily configure (duplicate) the settings with which the wireless communication is stable. Further, as described above, the attachable/detachable external antennas 4a and 4b can be removed while the movable radiographing apparatus 1a is moved. Thus, the smooth movement of the movable radiographing apparatus 1a is not disturbed.

A configuration example of the control unit 21 will be briefly described below. A computer including a central processing unit (CPU), a random access memory (RAM), and a read only memory (ROM) is used as the control unit 21. The ROM stores a computer program for controlling the movable radiographing apparatus 1a. The CPU reads the computer program from the ROM and loads it in the RAM to execute the computer program. In this way, the computer functions as the control unit 21 and controls the components of the movable radiographing apparatus 1a to realize the foregoing processes and operations. In this case, the RAM functions as the storage unit 211. The movable radiographing apparatus 1a may further include a storage device, and a computer-readable computer program for controlling the movable radiographing apparatus 1a may be stored in the storage device. In this case, the storage device may be configured to function as the storage unit 211.

As described above, the external antennas 4a and 4b are attachable to and detachable from one or more connector units 31, 32, and 33 so that the wireless LAN communication can be performed with a stable radio wave state. Furthermore, the external antennas 4a and 4b do not disturb the smooth movement of the movable radiographing apparatus 1a and the radiographing operation at the time of moving the movable radiographing apparatus 1a and at the time of performing the radiographing operation. Further, since the antenna information can be stored in the storage unit 211 of the control unit 21, the user can easily duplicate the communication situation of the wireless LAN in the previous radiographing by displaying on the GUI 23 the antenna information stored in the storage unit 211 of the control unit 21. Especially, the settings with which the wireless communication is stable are stored in the storage unit 211 so that the settings with which the wireless communication is stable can easily be configured (duplicate).

Figure 6:
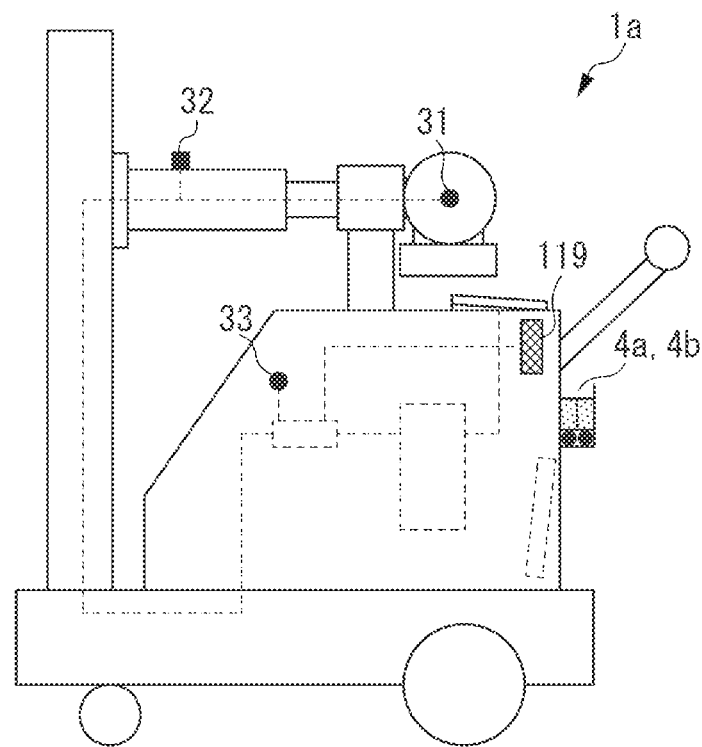
FIG. 6 is a schematic block diagram illustrating a movable radiographing apparatus including a non-detachable antenna, and connector units to and from which an external antenna is attachable and detachable.

While, in the present exemplary embodiment, an example the configuration is described in which all of the antennas used in the wireless communication are the attachable/detachable external antennas 4a and 4b, it is not limited to this configuration. For example, some of the plurality of antennas may include a non-removable antenna. The movable radiographing apparatus 1a may include a non-removable antenna 119 and the connector units 31, 32, and 33 to and from which the external antennas 4a and 4b are attachable and detachable. FIG. 6 is a block diagram illustrating a schematic configuration of such a movable radiographing apparatus 1a. In the movable radiographing apparatus 1a illustrated in FIG. 6, the connector units 31, 32, and 33 are provided at a plurality of positions. Further, the movable radiographing apparatus 1a includes the non-removable antenna 119. The user can detachably attach the external antennas 4a and 4b to the connector units 31, 32, and 33 as needed.

Further, the present invention is not limited to the exemplary embodiment described above. While, in the present exemplary embodiment, as an example of the wireless communication, the wireless LAN defined by the IEEE 802.11 protocol is described, the method and protocol of the wireless communication are not limited to those described above. Any other wireless communication that uses antennas may be employed. Further, the number of the connector units 31, 32, and 33 to and from which the external antennas 4a and 4b are attachable and detachable is not limited to three. The connector unit needs to be provided at one or more positions, or more preferably at two or more positions. In other words, the connector unit may be provided at one or two positions, or at four or more positions. Further, the attachable/detachable external antennas 4a and 4b are not limited to the dipole antenna 4a and the diversity antenna 4b. Various types of omnidirectional antennas and directional antennas can be used as the external antennas 4a and 4b. Further, the external antennas 4a and 4b may be an antenna with a cable or an antenna without a cable. For example, a small monopole antenna with a cable can be used as the omnidirectional antenna with a cable. Further, the number of the access points 22 of the wireless LAN is not limited to one. Two or more access points 22 may be included. Further, a place to which the movable radiographing apparatus 1a is to be moved (place where the radiographing is to be performed) is not limited to the hospital room in which the subject M is, and may be, for example, a surgery room or an emergency room.

Further, the antenna information to be added to the image data is not limited to the information about the frequency of the wireless LAN, channels, radio field intensity of the wireless LAN, positions of the connector units 31, 32, and 33 to which the external antennas 4a and 4b are attached, and the types and orientations of the external antennas 4a and 4b. The antenna information may be some of the plurality pieces of information described above. Further, the above-described configuration in which the antenna information is added to the image data of the captured radiographic image is not limited thereto. For example, the control unit 21 may manage the antenna information as separate data from the image data. Further, the above-described configuration in which the information about the positions of the connector units 31, 32, and 33 to which the attachable/detachable external antennas 4a and 4b are attached and the types and orientations of the external antennas 4a and 4b in the antenna information are set using the GUI 23 is not limited thereto. For example, scales for measuring the orientations of the attached external antennas 4a and 4b may be provided near the connector units 31, 32, and 33, and the user may read the figures indicated by the scales and input the read figures using the GUI 23.

Figure 7:
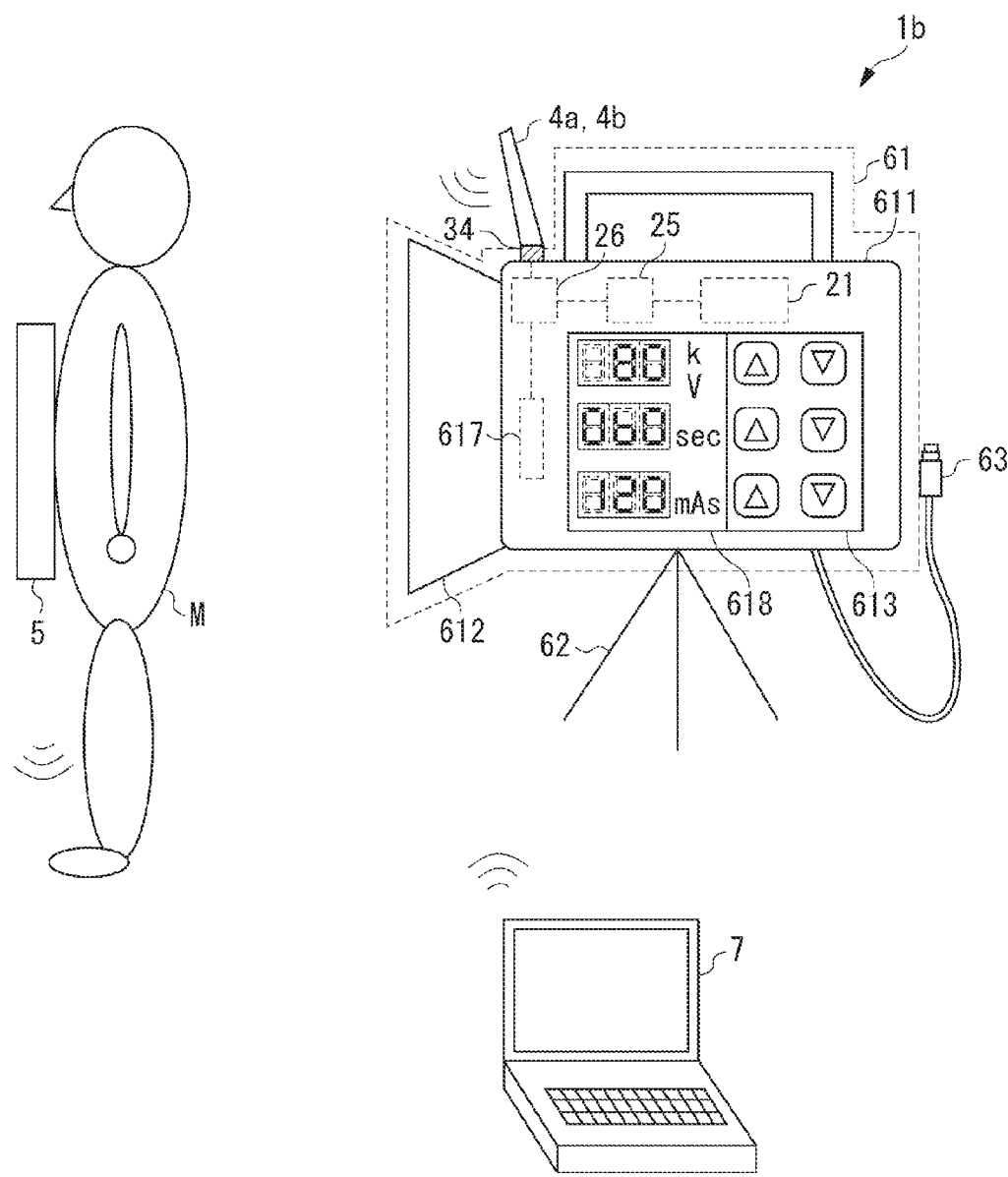
FIG. 7 is a schematic block diagram illustrating a movable radiation generating apparatus according to a second exemplary embodiment.

Next, a second exemplary embodiment of the present invention will be described below. Components that are similar to those in the first exemplary embodiment are given the same reference numerals, and description of the components is omitted. In the second exemplary embodiment, a movable radiation generating apparatus 1b having a wireless LAN function will be described. FIG. 7 is a block diagram illustrating a schematic configuration of the movable radiation generating apparatus 1b according to the present exemplary embodiment. In the present exemplary embodiment described below, the radiographing is performed at home.

The movable radiation generating apparatus 1b includes a radiation generating device 6. Further, a wirelessly communicable FPD 5 and a portable computer (hereinafter "PC 7") are used in the radiographing. The FPD 5 and the PC 7 have a wireless communication function and a built-in antenna (not illustrated), and can communicate wirelessly. The radiation generating device 6 includes a radiation generating unit 61 including a radiation source, a tripod 62 for fixing the radiation generating unit 61, and a radiation irradiation switch 63, which is an operation member for irradiation with radiation. The radiation generating unit 61 includes a housing 611 and a collimator 612. The housing 611 houses a radiation tube (not illustrated), which is a radiation source. The collimator 612 narrows down the radiation irradiation field. In FIG. 7, the portion surrounded by dotted lines indicates the radiation generating unit 61. On the front surface of the housing 611, a display unit 618, a setting unit 613, which is an example of an operation unit, and a connector unit 34 are provided. The display unit 618 displays radiographing conditions. The setting unit 613 is an example of an operation unit for setting the radiographing conditions. External antennas 4a and 4b for wireless communication are attachable to and detachable from the connector unit 34. In FIG. 7, a state in which a dipole antenna 4a (refer to FIG. 2A) is detachably attached as the external antenna for wireless communication to the connector unit 34. A control unit 21 for controlling the radiation generating unit 61, an access point 22 of the wireless LAN, and a built-in antenna 617 for wireless communication are arranged within the housing 611. The control unit 21 is connected to the access point 22 via the wired LAN. The access point 22 is connected to the built-in antenna 617 and the connector unit 34 by wired connection using a coaxial cable, etc. The tripod 62 is an example of a fixing member for fixing the radiation generating unit 61. The fixing member is not limited to the tripod 62 and may be any member that can fix the radiation generating unit 61. In other words, the movable radiation generating apparatus 1b may be configured to include any fixing member that can fix the radiation generating unit 61.

When performing the radiographing, the user operates the tripod 62 and/or the collimator 612 to locate the movable radiation generating apparatus 1b at a position from which the radiation can be applied to a site to be radiographed of the subject M. Further, the user locates the FPD 5 at a position where the radiation having passed through the subject M enters. In this state, the user stores antenna information in the storage unit 211 of the control unit 21. The antenna information includes information about the frequency of the wireless LAN, channels, radio field intensity of the wireless LAN, the position of the connector unit 34 to which the attachable/detachable external antennas 4a and 4b are attached, and the types and orientations of the attached external antennas 4a and 4b. While, in the present exemplary embodiment, the configuration is described in which the connector unit 34 is provided at one position of the movable radiation generating apparatus 1b, the number of the connector unit 34 is not limited. The connector unit 34 only needs to be provided at one or more positions.

The storage of the antenna information will be described below. The user operates the PC 7 to give an instruction to measure the radio field intensity of the wireless LAN of each channel. In response to the instruction to measure the radio field intensity of the wireless LAN of each channel, the control unit 21 controls the access point 22 to measure the radio field intensity of the wireless LAN of each channel and returns the measurement results to the PC 7. The control unit 21 periodically repeats execution of the foregoing process.

FIG. 8 illustrates an example of a table illustrating the radio field intensities of the wireless LAN of the respective channels received by the PC 7. The PC 7 displays such a table on its display. In the table, "CHANNEL" and "ESSID" respectively indicate the channel and the ESSID name of the wireless LAN having received the highest radio field intensity. Further, "dBm" indicates the radio field intensity of the channel. "PORT01" indicates the ESSID name in the wireless LAN communication among the FPD 5, the movable radiation generating apparatus 1b, and the PC 7. "OTHER10," "OTHER11," "OTHER12," and "OTHER13" indicate ESSID names of wireless apparatuses having no relation to the FPD 5, the movable radiation generating apparatus 1b, and the PC 7. Further, a graph plotted based on the table illustrated in FIG. 8 is as illustrated in FIG. 3.

A change in the orientations of the external antennas 4a and 4b made by the user causes a change in the radio field intensity of the wireless LAN of the channels in the table. In a case where the radio field intensity of "PORT01" is sufficiently high, the user may remove the external antennas 4a and 4b from the connector unit 34. In this case, the wireless LAN communication is performed using the built-in antenna 617 alone. On the other hand, if the radio field intensity of the PORT01 in the state in which the external antennas 4a and 4b are attached is low, the diversity antenna 4b illustrated in FIG. 2B may be attached to the connector unit 34. Then, the user may set the types and orientations of the external antennas 4a and 4b to realize stable wireless communication. Thereafter, the user stores in the PC 7 the information about the frequency of the wireless LAN illustrated in FIG. 8, channels, and the radio field intensity of the wireless LAN. Further, as described above with reference to FIG. 4, the user stores in the PC 7 the information about the position of the connector unit 34 to which the external antennas 4a and 4b are attached and the types and orientations of the attached external antennas 4a and 4b.

The setting of the subject information and the radiographing conditions will be described below. The user operates the PC 7 to set the subject information, a residence where the subject lives, a site to be radiographed, radiographing conditions, etc. When the user performs the operation to set the radiographing conditions, the PC 7 communicates wirelessly with the movable radiation generating apparatus 1b to set the radiographing conditions of the movable radiation generating apparatus 1b. Then, the control unit 21 displays the set radiographing conditions on the display unit 618. To change the radiographing conditions set with respect to the movable radiation generating apparatus 1b, the user operates the setting unit 613. Then, the control unit 21 changes the radiographing conditions displayed on the display unit 618 according to the operation. Further, the movable radiation generating apparatus 1b and the PC 7 communicate via the wireless LAN, and the control unit 21 notifies the PC 7 of the radiographing conditions changed by the operation performed using the setting unit 613.

When the operations to set the subject information and the radiographing conditions are completed, the user performs a radiographing operation. More specifically, the user observes the subject M and presses the radiation irradiation switch 63 at a suitable timing. Then, the control unit 21 controls the radiation generating unit 61 to emit radiation from the radiation source. The FPD 5 detects the radiation having passed through the subject M to generate image data of a radiographic image, and transfers the generated image data of the radiographic image to the PC 7 via the wireless LAN. Upon receiving the image data of the radiographic image captured by the FPD 5, the PC 7 performs image processing and the like on the received image data, and then displays the image data on its display. Further, if the user determines that the captured radiographic image is acceptable, the user performs an operation to add information such as the subject information, the residence address where the subject lives, the radiographed site, the radiographing conditions, etc. and antenna information to the image data of the radiographic image. The antenna information includes information about the frequency of the wireless LAN, channels, radio field intensity of the wireless LAN, the position of the connector unit 34 to which the attachable/detachable external antennas 4a and 4b are attached, and the types and orientations of the attached external antennas 4a and 4b. Then, the PC 7 stores (saves) in the built-in storage medium the image data of the radiographic image to which the foregoing information is added.

Upon returning to a hospital or the like after the radiographing, the user connects the PC 7 to the in-hospital network 9, and transfers the image data of the captured radiographic image to the PACS, etc. so that in the next radiographing of the same subject, the user can refer to the added information included in the previously-captured radiographic image and/or the image data of the radiographic image by downloading the added information from the in-hospital network 9 to the PC 7. Thus, the settings of the attachable/detachable external antennas 4a and 4b can be configured with ease in the second and subsequent radiographing.

Figure 9:
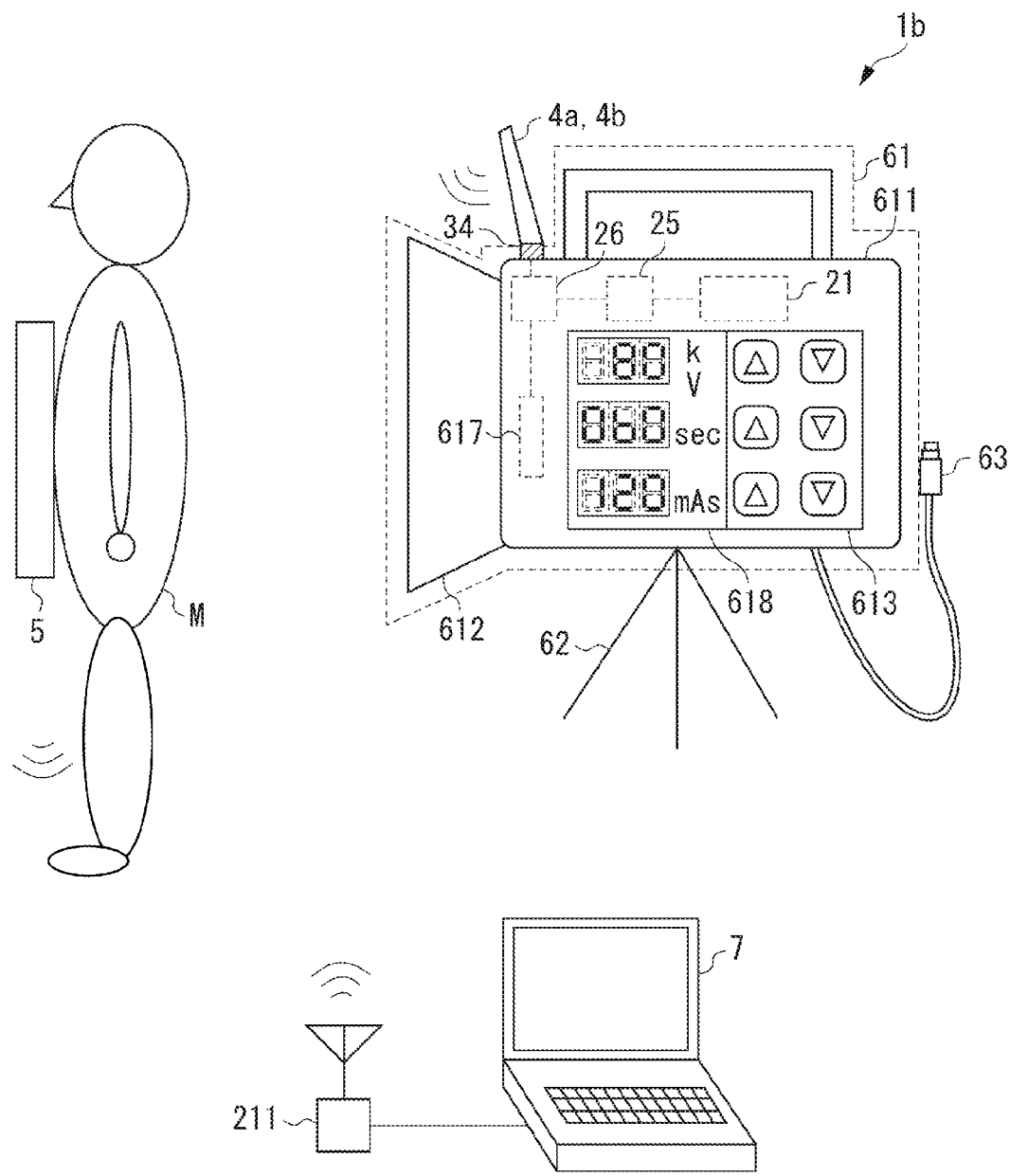
FIG. 9 is a schematic block diagram illustrating a movable radiation generating apparatus including a radiation generating unit without an access point.

While, in the present exemplary embodiment, the configuration of the movable radiation generating apparatus 1b including the access point 22 of the wireless LAN is described, it is not limited thereto. For example, as illustrated in FIG. 9, the movable radiation generating apparatus 1b may include no access point 22 of the wireless LAN while including a communication control unit 25 and an antenna switching unit 26. In place of the access point 22, the communication control unit 25 controls the wireless communication performed via the built-in antenna 617 or the external antennas 4a and 4b. For example, various types of wireless communication modules can be used as the communication control unit 25. The antenna switching unit switches between the built-in antenna 617 and the external antennas 4a and 4b according to the control by the communication control unit 25. More specifically, in a case where the external antennas 4a and 4b are attached, the antenna switching unit 26 selects the external antennas 4a and 4b to perform wireless communication. On the other hand, in a case where the external antennas 4a and 4b are not attached, the antenna switching unit 26 selects the built-in antenna 617. Further, the antenna switching unit 26 may select, according to the control by the PC 7, one of the external antennas 4a and 4b and the built-in antenna 617 that can realize more stable wireless communication. Further, in a case where the wireless communication is not stable enough although the external antennas 4a and 4b are attached, the antenna switching unit 26 may switch the external antennas 4a and 4b and the built-in antenna 617 to use all of the external antennas 4a and 4b and the built-in antenna 617 in the wireless communication. The access point 22 of the wireless LAN may be connected to the PC 7 by wired connection. Further, while, in the present exemplary embodiment, the radiographing performed at home is described, it is not limited thereto, and the present exemplary embodiment is also applicable to emergency medical treatment outside a hospital, etc.

While the exemplary embodiments of the present invention have been described above, the above-described exemplary embodiments are mere examples of implementation of the present invention, and it is to be understood that the present invention is not limited to the above-described exemplary embodiments. The present invention can be implemented in various forms without departing from the spirit or scope of the invention.

For example, while, in the exemplary embodiments, the movable radiographing apparatus and the movable radiation generating apparatus that are communicable via the wireless LAN as the movable radiographing apparatus having the wireless communication function, are described, the present invention is not limited thereto. Further, the wireless communication method is not limited to the wireless LAN. The present invention is applicable to any movable radiographing apparatus having a wireless communication function.

The present invention is suitable for wirelessly communicable movable radiographing apparatuses. The present invention is suitable especially for radiographing apparatuses such as movable medical radiographing apparatuses and industrial non-destructive testing apparatuses. According to the exemplary embodiments of the present invention, the external antennas do not disturb the operation and movement of the radiographing apparatus while stable wireless communication is realized. Furthermore, the wireless communication environment of the previous radiographing can easily be duplicated in the second and subsequent radiographing.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-102586 filed May 16, 2014, which is hereby incorporated by reference herein in its entirety.

What is claimed is:

1. A movable radiographing apparatus having a wireless communication function, comprising:
   a radiation generating unit including a radiation source;
   an arm portion configured to support the radiation generating unit;
   a support pillar configured to support the arm portion;
   a moving unit configured to support the support pillar and including an operation unit to be operated by a user; and
   a plurality of connector units each configured to receive therein a removable external antenna which is for wireless communication between the movable radiographing apparatus and a flat panel detector,
   wherein the connector units are provided on at least two of the radiation generating unit, the arm portion, the support pillar, and the moving unit, and
   wherein the external antenna is attachable to any one of the connector units.

2. The movable radiographing apparatus according to claim 1, further comprising:
   a communication control unit; and
   an antenna switching unit, wherein one of the connector units is connected by wired connection to the antenna switching unit, and the antenna switching unit is connected by wired connection to the communication control unit.

3. The movable radiographing apparatus according to claim 1, further comprising an access point for wireless communication,
wherein each one of the connector units is connected by wired connection to the access point.

4. The movable radiographing apparatus according to claim 1, wherein the external antenna is an omnidirectional antenna or a directional antenna configured to be attachable to and detachable from any one the connector units.

5. The movable radiographing apparatus according to claim 1, wherein the external antenna is an antenna with a cable or an antenna without a cable configured to be attachable to and detachable from any one of the connector units.

6. The movable radiographing apparatus according to claim 1, further comprising:
a unit configured to set antenna information including at least one of information about a position of one of the connector units to which the external antenna is attached, a type of the attached external antenna, and an orientation of the attached external antenna;
a storage unit configured to store the set antenna information; and
a display unit configured to display the set antenna information or the stored antenna information.

7. The movable radiographing apparatus according to claim 1, further comprising:
a unit configured to measure a radio field intensity of wireless communication in a state in which the external antenna is attached to one of the connector units for wireless communication with the flat panel detector for the capturing of a radiographic image;
a storage unit configured to store the measured radio field intensity; and
a display unit configured to display the measured radio field intensity or the stored radio field intensity.

8. The movable radiographing apparatus according to claim 1, further comprising a storing unit configured to store the external antenna in a state in which the external antenna is detached from the connector units and is not in wireless communication with the flat panel detector.

9. A movable radiation generating apparatus having a wireless communication function, comprising:
a radiation generating unit including a radiation source;
a moving unit including an operation unit to be operated by a user to activate the radiation source; and
a plurality of connector units configured to detachably connect to an external antenna which is for wireless communication with a flat panel detector,
wherein the connector units include at least one connector unit provided at a position of the radiation generating unit and one connector unit provided at a position of the moving unit, and
wherein the external antenna is attachable to and removable from any one of the connector units.

* * * * *